United States Patent
Nacson et al.

(10) Patent No.: US 9,170,232 B2
(45) Date of Patent: Oct. 27, 2015

(54) SUBSTANCES DETECTION SYSTEM AND METHOD

(71) Applicant: Teknoscan Systems Inc., Vaughan (CA)

(72) Inventors: Sabatino Nacson, Thornhill (CA); Aleksandar Crnatovic, Toronto (CA); George Wiseman, Richmond Hill (CA)

(73) Assignee: Teknoscan Systems Inc., Vaughan, Ontario (CA)

( * ) Notice: Subject to any disclaimer, the term of this patent is extended or adjusted under 35 U.S.C. 154(b) by 0 days.

(21) Appl. No.: 14/397,087

(22) PCT Filed: Apr. 26, 2013

(86) PCT No.: PCT/CA2013/000412
§ 371 (c)(1),
(2) Date: Oct. 24, 2014

(87) PCT Pub. No.: WO2013/159204
PCT Pub. Date: Oct. 31, 2013

(65) Prior Publication Data
US 2015/0160161 A1    Jun. 11, 2015

Related U.S. Application Data

(60) Provisional application No. 61/638,919, filed on Apr. 26, 2012.

(51) Int. Cl.
*B01D 59/44* (2006.01)
*H01J 49/40* (2006.01)
(Continued)

(52) U.S. Cl.
CPC .......... *G01N 27/622* (2013.01); *H01J 49/0409* (2013.01)

(58) Field of Classification Search
USPC ......... 250/281–283, 286–290, 293, 295, 324, 250/325, 339.13, 379, 382; 73/1.06, 19.02, 73/23.22, 23.41, 863, 863.12; 436/161, 436/167; 324/464; 422/89
See application file for complete search history.

(56) References Cited

U.S. PATENT DOCUMENTS

| 3,699,333 A | 10/1972 | Cohen et al. |
| 5,027,643 A | 7/1991 | Jenkins |

(Continued)

FOREIGN PATENT DOCUMENTS

| CA | 2132607 A1 | 3/1995 |
| CA | 2218785 C | 4/1998 |

(Continued)

OTHER PUBLICATIONS

Han et al., "Continuous Preconcentrator for Trace Gas Analysis," Recent Patents on Mechanical Engineering 2009, vol. 2, No. 3, pp. 214-227.

(Continued)

*Primary Examiner* — Bernard E Souw
(74) *Attorney, Agent, or Firm* — Vidas, Arrett & Steinkraus

(57) ABSTRACT

A system and methodology for the detection of threat substances is described. The detector system consists of a method to evaporate the sample into a primary separator and thermal release of trapped target materials into a secondary separator like conventional GC. The GC column is thermally ramped to elute all substances and the end of the column terminates into an atmospheric pressure chemical ionization source of an axial ion mobility spectrometer (AIMS). Both polarity ions are pulsed into a single construction separator tube at different timing. Their arrival time is detected on a collector plate, which allows registering their ion mobility spectra of both polarities for a single GC peak.

11 Claims, 5 Drawing Sheets

(51) Int. Cl.
*H01J 49/00* (2006.01)
*G01N 27/62* (2006.01)
*H01J 49/04* (2006.01)

(56) References Cited

U.S. PATENT DOCUMENTS

| | | | |
|---|---|---|---|
| 5,200,614 A | | 4/1993 | Jenkins |
| 5,405,781 A * | | 4/1995 | Davies et al. .................. 436/52 |
| 5,491,337 A | | 2/1996 | Jenkins et al. |
| 6,124,592 A | | 9/2000 | Spangler |
| 6,407,382 B1 | | 6/2002 | Spangler |
| 6,593,567 B1 | | 7/2003 | Abdel-Rahman |
| 6,765,198 B2 | | 7/2004 | Jenkins et al. |
| 7,057,168 B2 | | 6/2006 | Miller et al. |
| 7,081,618 B2 | | 7/2006 | Laprade |
| 7,528,367 B2 | | 5/2009 | Haigh |
| 7,623,234 B2 | | 11/2009 | Puzey |
| 7,714,284 B2 | | 5/2010 | Miller et al. |
| 7,985,949 B2 * | | 7/2011 | Rodier ......................... 250/282 |
| 8,067,731 B2 * | | 11/2011 | Matyjaszczyk et al. ...... 250/295 |
| 8,952,321 B2 | | 2/2015 | Barket, Jr. et al. |
| 2002/0060290 A1 * | | 5/2002 | Pham ........................... 250/282 |
| 2002/0134933 A1 | | 9/2002 | Jenkins et al. |
| 2005/0051719 A1 | | 3/2005 | Miller |
| 2005/0173629 A1 | | 8/2005 | Miller et al. |
| 2008/0173809 A1 * | | 7/2008 | Wu .............................. 250/283 |
| 2009/0032701 A1 * | | 2/2009 | Rodier ......................... 250/282 |
| 2009/0113982 A1 | | 5/2009 | Hodyss et al. |
| 2009/0224150 A1 * | | 9/2009 | Matyjaszczyk et al. ...... 250/282 |
| 2011/0133078 A1 | | 6/2011 | Barket et al. |
| 2013/0037710 A1 * | | 2/2013 | Wu .............................. 250/287 |
| 2013/0306855 A1 * | | 11/2013 | Raptakis et al. ............. 250/282 |

FOREIGN PATENT DOCUMENTS

| | | |
|---|---|---|
| CA | 2474566 A1 | 8/2003 |
| CA | 2650240 A1 | 11/2007 |
| CN | 102016561 A | 4/2011 |

OTHER PUBLICATIONS

PCT International Search Report and Written Opinion for PCT application PCT/CA2013/000412, mailed on Aug. 21, 2013; 21 pgs.

* cited by examiner

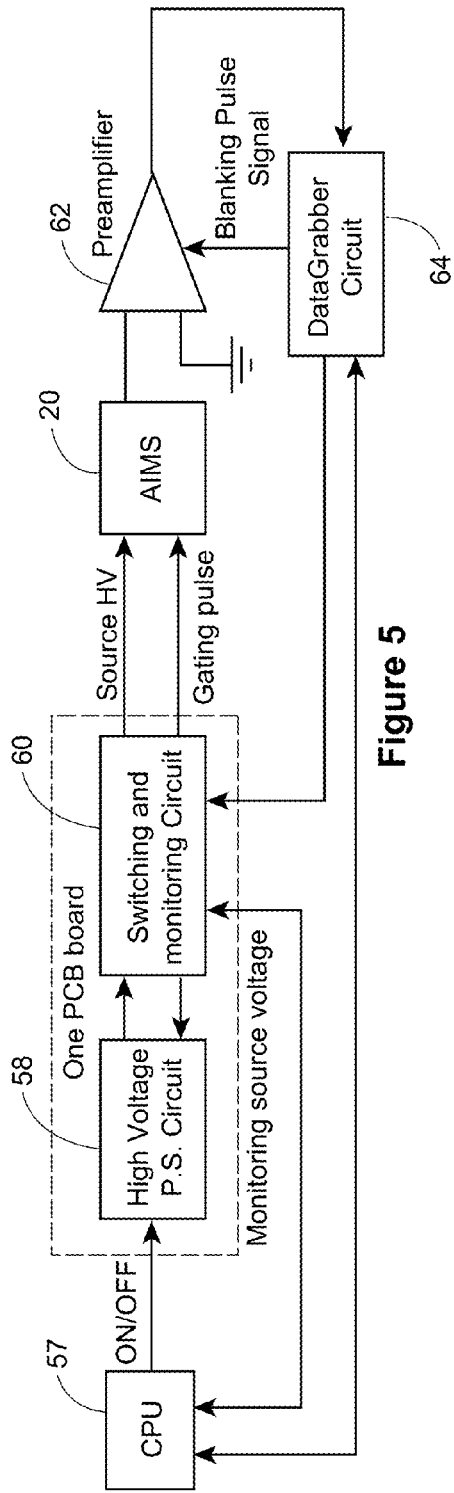
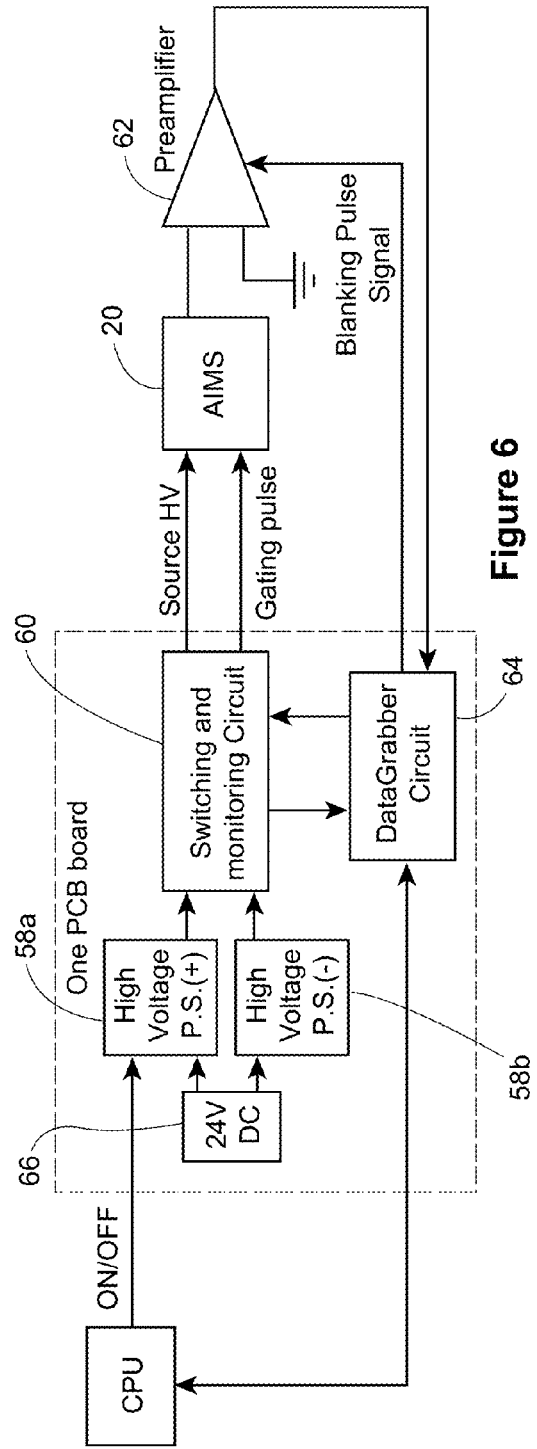

SUBSTANCES DETECTION SYSTEM AND METHOD

CROSS REFERENCE TO RELATED APPLICATIONS

This application is the national stage of International (PCT) Application No. PCT/CA2013/000412, filed Apr. 26, 2013, which claims the benefit of and priority to U.S. Provisional Patent Application Ser. No. 61/638,919, filed Apr. 26, 2012, the entire contents of each of which are herein incorporated by reference.

FIELD OF THE INVENTION

This invention relates to the field of substance detection (for example, explosives, narcotics, chemical warfare agents, environmental pollutants), which are typically but not necessarily threat substances.

BACKGROUND OF THE INVENTION

The increasing terrorist threat internationally has made it crucial to detect all kinds of explosives and other threat substances in order to provide security for important locations such as airports, border crossings, embassies, seaports, governmental buildings, power stations or transportation systems. A number of techniques for detecting threat substances are known, such as X-ray screening, fluorescence quenching, neutron and gamma-ray spectroscopy, LC-MS, UV gated Raman spectroscopy, laser induced breakdown spectroscopy, electrochemical and immunosensors, chemiluminescence, SPME-HPLC, GC-ECD, GC-SAW devices, GC-differential mobility spectrometer. More recently, metal oxide semiconductor (MOS) nanoparticle sensors have been used for the detection and discrimination of low concentrations of explosives.

Ion mobility spectrometry (IMS) has been shown over the past 20 years to be a reliable method for trace detection of explosives, drugs, chemical warfare agents, toxic industrial chemicals and various organic environmental pollutants, due to its low detection limit, relatively fast response, hardware simplicity, and portability. IMS-based equipment is presently used in vulnerable places, such as airports, for screening of both people and carry-on luggage.

Although IMS technology has been successful in many areas, it is undesirably limited in cases where the sample material is presented in complex matrices. Under these conditions, when other materials are liberated with the analytes of interest, those other materials can selectively compete in the ionization process. Their ionization levels may be less than those for the analytes of interest, so they competitively react in the ionization process and greatly reduce the sensitivity and selectivity of the IMS.

IMS is a gas-phase ion separation technique that operates under atmospheric pressure. A drift tube consisting of a reaction region and drift region is the main element of the IMS instrument. In conventional IMS instruments, the electric field is created by a series of conducting guard rings, and in more simplified drift tube designs the ion drift tube is formed of single-piece, conductive glass tube. This more recent drift tube design is disclosed in U.S. Pat. No. 7,081,618, which describes a reaction-ionization/drift tube chamber constructed with one or more single-piece conductive ceramic or glass tubes having specified conductivity. The glass tube or ceramic is used in place of the stack assemblies of metal and ceramic annular components that were typically used in previous drift tubes. This approach provides a simpler design, fewer parts and improved performance for fast switching of ion polarity during a scanning mode.

Ion mobility spectrometers for detection of explosives, narcotics and other contraband are disclosed in U.S. Pat. Nos. 3,699,333, 5,027,643, and 5,200,614. U.S. Pat. No. 5,491,337 shows still further improvements to ion trap mobility spectrometers and U.S. Pat. No. 6,690,005 describes a pulsing mechanism for ions entering the rings-stack drift tube with front trapping capability and switching of ion polarity entering the drift chamber. U.S Patent application 2002/0134933 provides a method for detecting both positive and negative mobility spectra wherein the first and second selected switching times are less than 20 msec and 15 msec, respectively, with a transition time of less than 5 msec.

U.S. Pat. No. 7,528,367 describes an ion mobility spectrometer with an inlet that communicates to an ionization chamber and a drift chamber. Stacked grid electrodes with applied potential hold ions between them until they are pulsed into the drift chamber. This patent claims sharper peak shape and improved resolution. U.S. Pat. Nos. 6,124,592 and 6,407,382 describe methods to separate and store ions by exploiting mobility characteristics of the ions by applying an electric field to trap the volume of ions prior to pulsing them into the ring stacked drift chamber. US application 2009/0113982 discloses a multi-dimensional detection system based on the ultraviolet detection of molecules produced in the thermal decomposition of explosive compounds separated by gas chromatography.

Meanwhile, the combination of GC and IMS has been established for the use of the IMS as a detector to the effluent from a GC, wherein the IMS has been interfaced to the GC effluent column and operates continuously and is used no differently than other conventional GC detectors such as flame photometric, flame ionization and electron capture detectors.

SUMMARY OF THE INVENTION

What is desired is a system and/or method having better performance, simpler assembly, reduced cost and/or greater reliability for field deployment, than the prior art. Also, the present invention will preferably provide sufficient selectivity and specificity for analyzing the complex chemical matrix that is normally encountered in sampling maritime containers, air cargo, luggage and the like.

In an aspect of the invention, a GC is used as a tool to separate out predetermined analytes of interest to be selectively fed to the IMS on an intermittent and temporally separated basis. Thus, samples are cleaned up prior to analysis by IMS, as opposed to using an IMS as an alternative detector to a constant effluent flow from a GC separation column. The GC acts as a pre-analysis separator such that effluent is introduced to the IMS only when certain predetermined elution conditions have been met. Furthermore, detection criteria may be selectively set to alarm when both positive and negative IMS peaks are detected at a certain ratio for a specific elution time.

The advantages of IMS detection, such as high sensitivity, good specificity, and fast detection rates can be more effectively utilized when the sample is preconditioned. A major difficulty with the use of IMS under field conditions is the heavily contaminated samples and complex chemical matrices often found in the field. These can cause detector overload and system contamination. Such conditions occur, for example, in forensic investigations following bombing incidents, and in the search of shipping containers for drugs and explosives. The problem arises within the ionization process where the background contaminants which are present in much greater abundance than the analytes of interest dominate the ionization process and preferentially take the available electrons or charge reservoir for ionization to the detriment of the analytes, such that limits of detection and selectivity are significantly degraded.

This effect is shown in equation (1) where the available charge reservoir in the ionization source of the IMS is affected by numerous compounds entering the ionization process with different concentrations and affinity for electron charge.

$$[\text{Reagent Ions}]EAR = [A]EAA + [B]EAB + [C]EAC+ \quad (1)$$

[R]=reagent ion reservoir concentration in the ionization source

EA=Electron affinity of compound A, B, C entering the source

[A]=Concentration of analyte of interest

[B], [C]=Concentration of contaminants in the sample

By pretreating the sample in the sample vaporization process, and separating it in a sample loop and in the GC column such that only analytes that are very close to those earmarked for detection are fed into the IMS, significant improvements in signal to noise ratio can result, and false alarm rates can be considerably reduced.

Chromatography is a very mature well established technique. The capillary columns contain liquid phases chemically bonded to the column walls. The passage of the vapour through the column is retarded to varying degrees depending upon carrier gas flow rates, column temperature and chemical properties of the compounds injected onto the column. Different chemicals will travel through the GC at different rates and emerge at different times. In the preferred form of the invention, the eluent portion of interest is taken to the detector, by time separation, while other fractions are allowed to bypass the detector (preferably IMS) as needed. This prevents unwelcome competition in the ionization process and/or overloading of the detector.

In an aspect of the invention, a pre-separator is used after the desorber step. This allows venting of volatile contaminants in the sample and trapping of the analytes of interest. The temperature of the pre-separator is pulsed to expel the trapped analytes into the head of the GC column. The temperature of the column is ramped by applying power to the conducting tubing of the column to provide separation of various fractions of the pre-separated sample. The analytes of interest are then introduced into the ionization source of the AIMS at different intervals.

In an aspect of the invention, the substances detection system includes, optionally, a desorption apparatus which receives the sample, and operates to clean the sample by removing volatile compounds not of interest while vaporizing remaining potential analytes of interest from the sample, which travel to a pre-separator. The pre-separator functions to release potential analytes of interest from the cleaned sample sequentially, separated in time. The potential analytes of interest are delivered sequentially to an IMS detector for short cycle processing, are processed there, and analytes of interest, if any, provisionally identified.

Simultaneously, potential analytes of interest are also delivered to a GC for conditioning and/or further separating (long cycle). Once separated, the potential analytes of interest are delivered to the IMS detector having been separated and cleaned more thoroughly than the short cycle potential substances of interest. Thus, if the short cycle identifies a substance of interest, that identification can either be confirmed as correct, or as a false alarm, by the long cycle. The long cycle result is more reliable because the long cycle provides a more thoroughly conditioned and separated sample to the detector.

Also, in an aspect of the invention, introductions of various chemical ionization reagents (CIR) used in the IMS into the ionization source with the effluents from the GC are timed to the particular GC peak of interest. Thus, when there is no GC peak, no CIR is being introduced at all. Also, each particular predetermined CIR used for a corresponding particular substance of interest is introduced only concurrently with the GC peak associated with that substance of interest.

In an aspect of the invention, there is provided system for detecting the presence of one or more predetermined analytes in a sample, wherein the predetermined analytes number two or more, the system comprising:

a temporal separation means for temporally separating the predetermined analytes within the sample;

an ion mobility spectrometer detector programmed to detect the predetermined analytes of interest in the sample;

wherein the temporal separation means is configured to deliver the analytes of interest one by one, separated in time, to the ion mobility spectrometer detector.

In an aspect of the invention, there is provided a method of detecting the presence of one or more predetermined analytes in a sample, wherein the predetermined analytes number two or more, the method comprising the steps of:

pre-separating the sample by temporally separating the predetermined analytes in the sample; then splitting the pre-separated sample into a bypass sample and a main sample; then delivering the bypass sample to the detector for preliminary detection of one or more predetermined analytes;

delivering the main sample to the gas chromatograph to further temporally separate predetermined analytes;

then delivering the further separated main sample to the detector to confirm or disconfirm detection of one or more predetermined analytes.

In an aspect of the invention, there is provided a method of detecting the presence of one or more predetermined analytes in a sample, wherein the predetermined analytes number two or more, the method comprising the steps of:

temporally separating potential predetermined analytes in the sample;

delivering the temporally separated potential predetermined analytes one-by-one to the ionization chamber of and IMS detector;

deploying chemical ionization reagent to the ionization chamber concurrently with the delivery of each potential predetermined analyte;

withholding chemical ionization reagent when there is no delivery of predetermined analyte to the ionization chamber occurring;

if one or more predetermined analytes is present, detecting their presence.

In an aspect of the invention, there is provided an apparatus for detecting the presence of one or more predetermined analytes in a sample, wherein the predetermined analytes number two or more, the apparatus comprising:

a detector configured to receive and detect the presence of predetermined analytes carried in a carrier gas;

a carrier gas generator, the generator comprising a single reservoir and configured to selectively operate in a gas delivery mode in which clean carrier gas is delivered to the detector and a cleaning mode in which the generator generates clean carrier gas for subsequent use in the detector;

wherein the detector and the generator and positioned in a common housing.

In an aspect of the invention, there is provided an apparatus for detecting the presence of one or more predetermined analytes in a sample, wherein the predetermined analytes number two or more, the apparatus comprising:

a detector configured to receive and detect the presence of predetermined analytes carried in a carrier gas;

a carrier gas generator, the generator comprising first and second reservoirs and configured such that the first reservoir operates in a gas delivery mode in which clean carrier gas is delivered to the detector while the second operates in a cleaning mode in which clean carrier gas is generated for subsequent use in the detector;

the generator being configured to switch the first reservoir to the cleaning mode and the second reservoir to the gas delivery mode wherein the detector and the generator and positioned in a common housing.

In an aspect of the invention, there is provided a detector for detecting the presence of one or more predetermined analytes in a sample, wherein the predetermined analytes number two or more, the detector comprising an IMS detector configured receive potential predetermined analytes from a GC during GC peaks, the detector being configured to simultaneously ionize the potential predetermined analytes positively and negatively, and to scan across the GC peaks to obtain both positive and negative scans across each GC peak.

BRIEF DESCRIPTION OF THE DRAWINGS

Reference will now be made, by way of example only, to preferred embodiments of the invention and in which:

FIG. 5 is a schematic representation of the detector circuitry;

FIG. 6 is a schematic representation of alternative detector circuitry; and

DETAILED DESCRIPTION OF THE PREFERRED EMBODIMENTS

Figure 1:
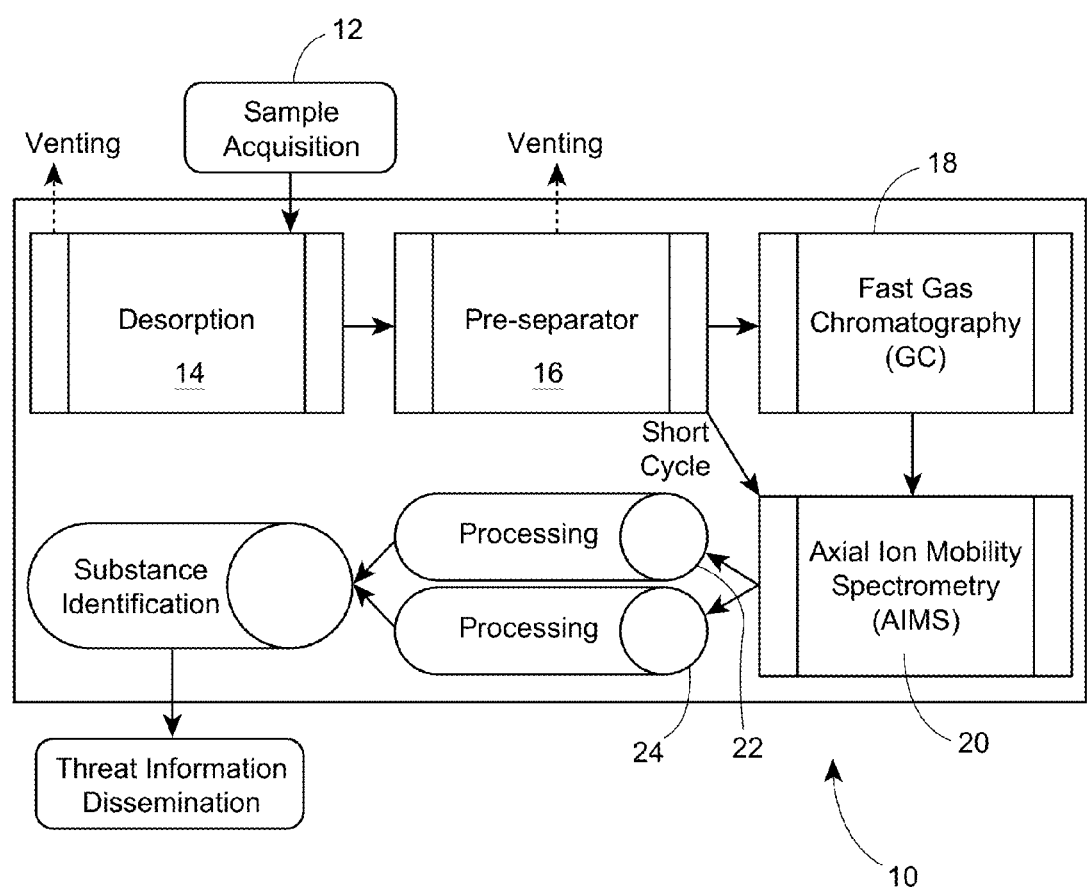
FIG. 1 is a schematic representation of the preferred analyser system.

Referring now to FIG. 1, a schematic representation of the preferred analyser system 10, according to an aspect of the invention, is shown. The sample 12 is acquired through interfacing with desorber 14. Desorber 14 communicates with pre-separator 16, which communicates both with GC 18, and AIMS 20. Processing means 22 and 24 are in communication with AIMS 20, and the outputs of means 22, 24 are used to identify substances of interest, after which identification information is disseminated. In the preferred embodiment, a carrier gas (discussed below) carries the sample from the desorber 14, to the pre-separator 16, the GC 18 and the AIMS 20.

The sample may, for example, be positioned on a sample collection slide, card or filter disk sized and configured to interface with the desorber 14. Preferably, the desorber 14 includes means for ramping up temperature upon receipt of a sample to evaporate volatile compounds not of interest, thus cleaning the sample. These volatile contaminants are preferably vented. As the temperature continues to rise, the cleaned sample is then evaporated and travels to the pre-separator 16. Preferably, the desorber 14 communicates with the pre-separator 16 via a six-port heated valve, which functions to keep the sample evaporated until it condenses in the pre-separator 16. The pre-separator 16 is kept cool while the sample is transferred from the desorber 14, so that the sample will condense and thus be trapped.

The pre-separator 16 preferably operates as follows. It is heated in a ramping fashion with power pulses ranging from 100-500 msec to assist in the thermal separation of different compounds based on their physical and chemical properties. Each compound will be released at a different temperature, and thus at a different time, creating a temporal separation between the individual predetermined analytes present. The pre-separator 16 also functions to release other volatile compounds not of interest that were not removed by the desorber 14, while separating in time the release of potential analytes of interest as the pulsed increase in temperature proceeds.

Thus, the desorber 14 and pre-separator 16 function to eliminate unwanted compounds and/or contaminants (such as volatile compounds), and thus to preselect for analysis compounds likely to be of interest.

Preferably, the pre-separated sample emerging from the pre-separator 16 is split into main and bypass samples. The bypass sample is carried directly to AIMS 20, permitting a faster analysis as a result of the GC step being skipped for the bypass sample. This faster analysis can, in the preferred embodiment, take about 20-30 seconds, providing a quick detection of threat substances followed by confirmation after GC analysis of the main sample is completed is completed. This offers flagging of the sample for further investigation and circumvents the need to call on dog screeners and other measures which will slow down air cargo movement, luggage or other items.

On the other hand, if the short cycle shows no detection, there is a strong likelihood that the sample is clean. Preparations can begin to test the next sample. In the unlikely event that the long cycle shows detection when the short cycle did not, the relevant object (e.g. shipping containers, luggage, etc.) can be extracted and dealt with accordingly.

Preferably, the main sample is carried to the GC, and the preferred GC operates to evaporate the main sample by upward ramping of temperature. The main sample molecules are preferably trapped by adsorption, condensation, surface interaction on a cooled trapping material consisting of an inert coated metal surfacelike GC liquid phase and other means of trapping molecules. The trap is resistively heated by applying power across its terminals to release trapped materials into the carrier gas and transfer the evaporated main sample into the analytical GC column. The preferred GC column can contains polar, semi-polar or non-polar bonded liquid phase for effective separation of explosives molecules like NG, DNT, TNT, PETN, RDX, TATP, HMTD, HMX, and narcotics like cocaine, heroin, amphetamines, methamphetamines and other illicit drugs. The GC may also be configured to work for other compounds, including but not limited to alkaloids from tobacco, and human odors like lactic and pyruvic acids. An example of GC based explosive detector is described by R.Batlle, et al., Anal.Chem.75, 3137 (2003), the disclosure of which is incorporated herein by reference.

Temperature ramping of the preferred GC column is accomplished by resistive heating of the column from 40 to 220 degrees Celsius, which allows separation of volatile and non-volatile (higher boiling point) compounds, typically in a span of 1-3 minutes. The initial temperature of the GC before heating is preferably maintained by an electrically driven cooling fan.

Figure 2:
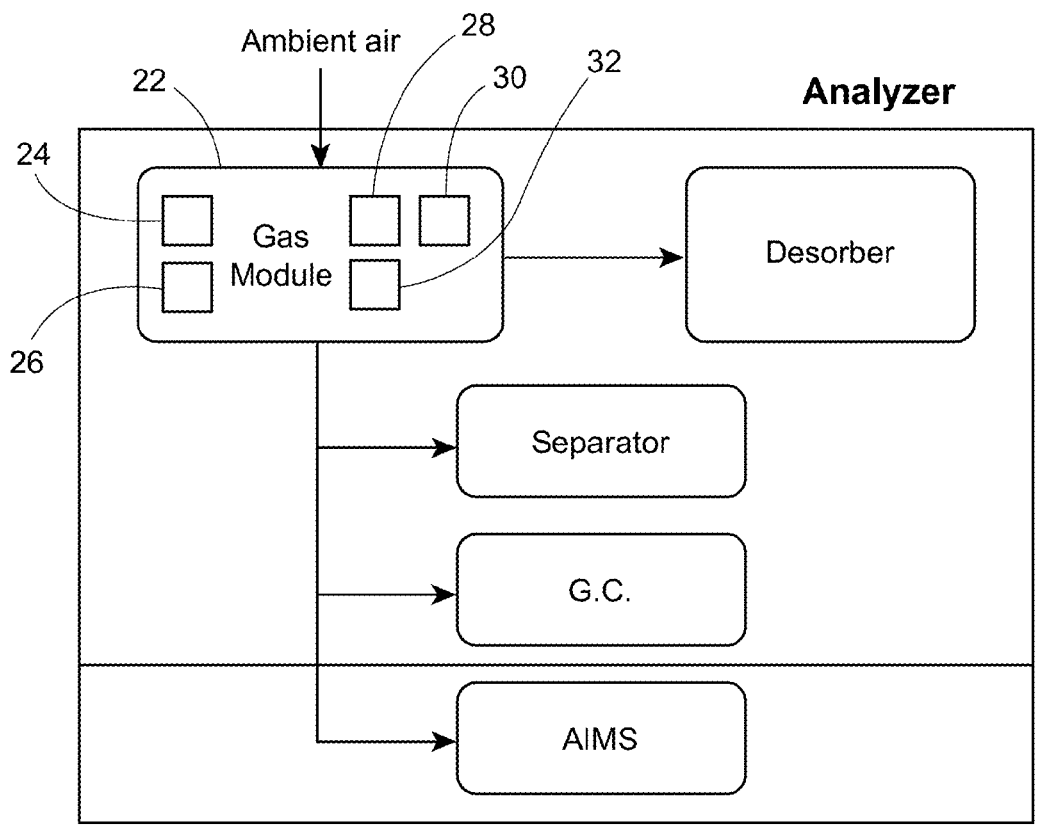
FIG. 2 is a schematic representation of a carrier gas generating means.

Referring now to FIG. 2, the carrier gas supply is preferably generated internally to the analyser system 10. Ambient air is delivered to a gas module 22 by a diaphragm pump 24, preferably internal to the module. The preferred gas module includes a reservoir 26 containing an adsorber in the form of moisture- and hydrocarbon-absorbing materials to clean the incoming ambient air, and a second reservoir 28 containing the same materials. Preferably, heating means associated with the second reservoir 28 function to heat it to 200 degrees Celsius. The two reservoirs are connected such that the second reservoir 28 is purged by a small stream of gas from the first reservoir 26. Subsequently, when the second reservoir is clean and the first dirty, the first is heated by heating means and purged by clean air from the second.

The preferred module further includes a timing circuit 30 and microprocessor 32 to control the use of each reservoir to supply clean gases. Preferably, the reservoirs are configured to clean the gas to a moisture content of less than 2 ppm and organic compounds content of less than 1 ppm. Also, preferably, the two reservoirs are contained in a common housing with the IMS.

It will be appreciated that in this configuration, either reservoir can be used to supply clean carrier gas to the system 10, including the desorber, pre-separator, GC and IMS.

In the preferred system, the gas module supplies clean carrier gas independently to the desorber 14, the the pre-separator 16, the GC 18 and the IMS 20. In each case, the carrier gas in used to advance the sample through each component, allowing for separation and/or analysis.

Figure 3:
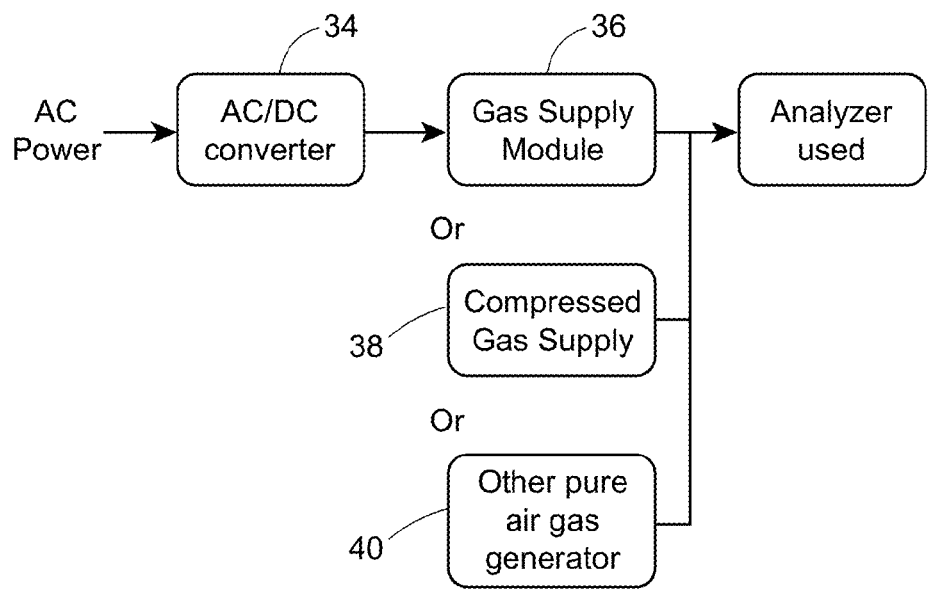
FIG. 3 is a schematic representation of an alternate carrier gas generating means.

In another embodiment of the invention (FIG. 3) there is an external carrier gas supplied from an external gas cylinder, reservoir assembly, or commercial zero air generator operated externally to the analyzer system. In such an embodiment, typically, an AC to DC converter 34 would provide DC to an external gas supply module 36 which would then deliver carrier gas to the system 10, preferably independently to each component as described above. In another embodiment a compressed gas supply 38 or other pure air gas generator 40 could be used instead of module 36.

Figure 4:
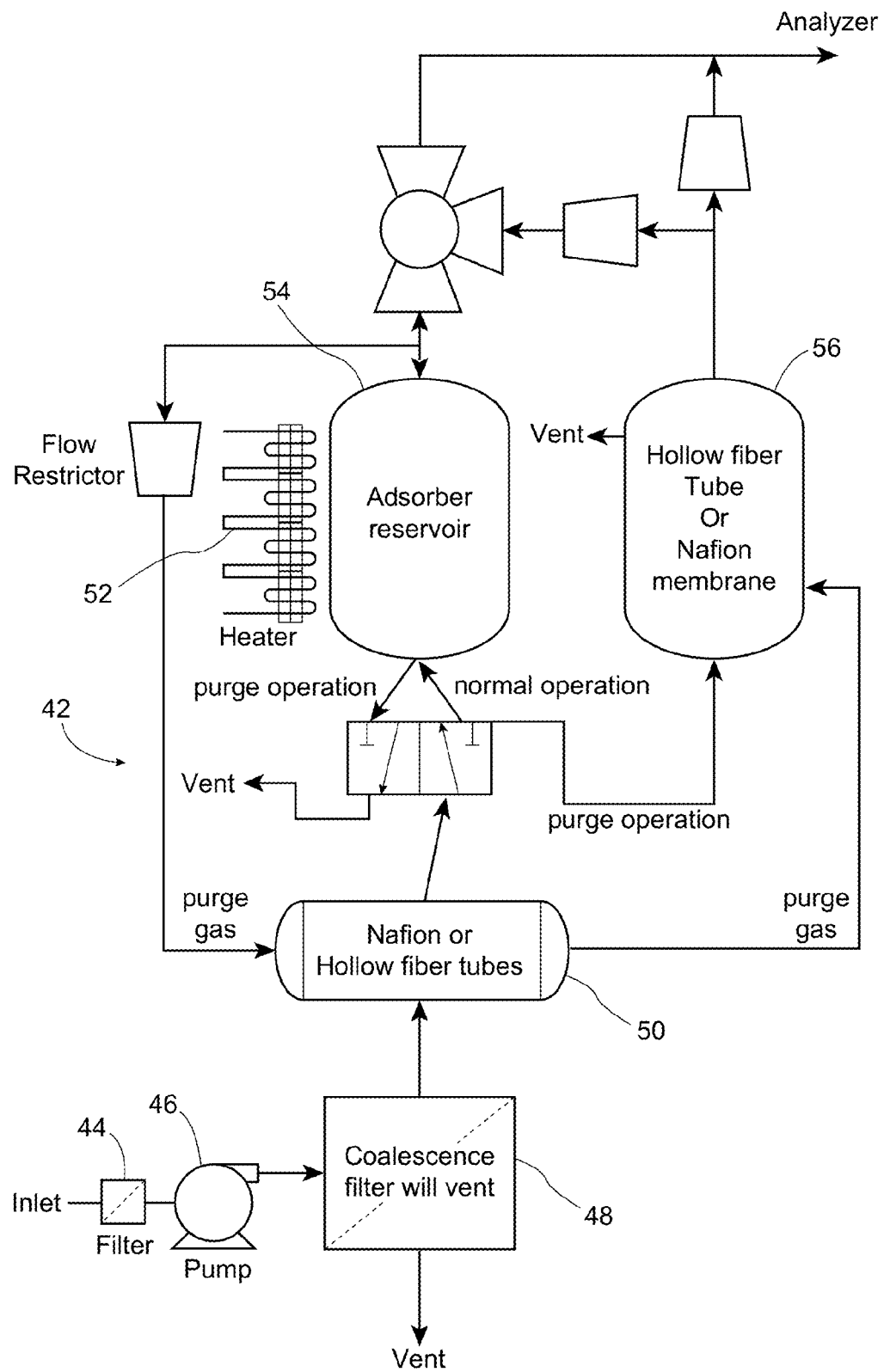
FIG. 4 is a schematic representation of another alternate carrier gas generating means.

In another embodiment, there is a gas supply module 42 (FIG. 4) comprising a single scrubbing tower that is capable of operating for 8-10 hours continuously and is heated to purge contaminants at the end of the cycle while the system is purged with a clean gas generated from use of membrane separator, hollow fiber air dryer modules offering high selectivity for water over air. Drying capability of 50-100 ppm of water and low hydrocarbon content can be achieved and sufficient to purge the reservoir for a full day operation. The module may be contained in a common housing with the IMS.

This module comprises of inlet filter 44, pump 46, coalescence filter 48, and fiber tubes dryer 50. Heater 52 heats reservoir 54 during the purge cycle, and dryer 56 cleans the gas, which is returned to reservoir 54 for use during normal operation. The module of FIG. 4 can supply clean carrier gas during normal operation, and taken offline for a purge cycle, typically after 8-10 hours of normal operation.

Preferably, the gas cleaning process will be microprocessor controlled, to provide precision control of the heating mechanism and purging cycle associated with cleaning the gas. Thus, preferably, the cleaned carrier gas has moisture content of less than 5 ppmv concentration, and hydrocarbon concentration of less than 1 ppmv. It is also preferred that the temperature control, gas flow and switching mechanisms of the adsorber enclosures are microprocessor controlled, which also allows for tracking the status of adsorber interaction time and use. This also allows precise conditions to be restored after a power failure.

Those skilled in the art will appreciate that the analysis using the IMS 20 involves ionization, typically both positive and negative, of the sample entering the IMS. IMS devices, in general terms, identify analytes of interest by measuring mobility of associated ions using a drift tube and detector. CIRs are deployed in the IMS' ionization chamber to facilitate ionization of the substances in the sample for detection.

The preferred embodiment of the system is configured to time the deployment of CIRs to be concurrent with the GC peaks of analytes of interest. This is in contrast to the prior art, in which CIRs are typically fed into the IMS constantly. In the preferred embodiment, then, CIRs are conserved, and wastage reduced, since CIRs are deployed only when needed for ionization. In the preferred embodiment, the microprocessor controlling the system 10 is programmed to as to release CIRs to the IMS only concurrently with GC peaks, that is, when potential analytes of interest are arriving for analysis. CIRs are preferably withheld during the absence of GCpeaks.

Referring now to FIG. 5, the IMS assembly preferably comprises a microprocessor or CPU 57 which is configured to switch on and off high voltage power supply 58 (HVPS). HVPS 58 and CPU 56 are operatively connected to switching and monitoring circuit 60, which is used by CPU 56 to monitor the voltage from the HVPS and to actually switch the voltage.

The AIMS 20 receives the switching voltage and provides the raw output used to calculate ion mobility and identify, if appropriate, analytes of interest. The output is amplified by a pre-amplifier 62 prior to delivery to a data grabber circuit 64. It will be appreciated that the pre-amplifier is vulnerable to damage from sudden large changes in electric field resulting from changes in polarity and ionization of the sample. Specifically, damage may result from sudden change of voltages and voltage surge on the guard electrode located in front of the IMS' Faraday collector plate. The system 10 is thus configured to provide a protective blanking pulse signal to the pre-amplifier timed to coincide with the changes in the electric field, thus preventing the aforementioned damage.

Circuit 60 preferably provides the high voltage polarity needed to operate the axial ion mobility spectrometer (AIMS) in one polarity and the appropriate gating pulse to introduce single polarity ions into the single glass or ceramic tube drift tube. The process is under CPU control. The signal generated at the preamplifier 62 is fed to the data grabber board 64 which controls the blanking pulse and feedback to the switching and monitoring circuit and to the CPU 56.

In the preferred embodiment, the circuit 60 comprises a half H instead of four H bridge, which offers a simpler and faster switching circuit capability over prior art.

Alternation between ion polarities is preferably governed by a timing circuit of duration varying from 100-500 msec, depending on the eluting GC peak from the chromatography column. In this mode, several positive ion scans are collected in one polarity and several negative ion scans are collected in the opposite polarity mode. This is possible because the GC peak is wide enough, and the switching frequency high enough, to provide sufficient numbers of data points associated with a single GC peak, for both positive and negative polarities. Preferably, a time gap is afforded between each polarity to allow stabilization of reagent ions and baseline.

In an alternate embodiment shown in FIG. 6, there are instead two HVPSs, 58a and 58b, one set to output positive voltage, and the other negative. In this embodiment, supplies 58a and 58b may both draw power from a 24 VDC power supply 66. The power supplies 58a and 58b themselves do not switch polarity. Rather, the circuit 60 switches between one HVPS and the other. Preferably, the data grabber rate is 100 k samples/sec or down to 10 microseconds/sample for improved peak resolution. The advantage of two separate high voltage power supply is ability to adjust the polarity independently for each HVPS. Also switch time is reduced, because polarity does not switch—preferably, switch time is reduced as low as 500 microseconds.

Figure 7:
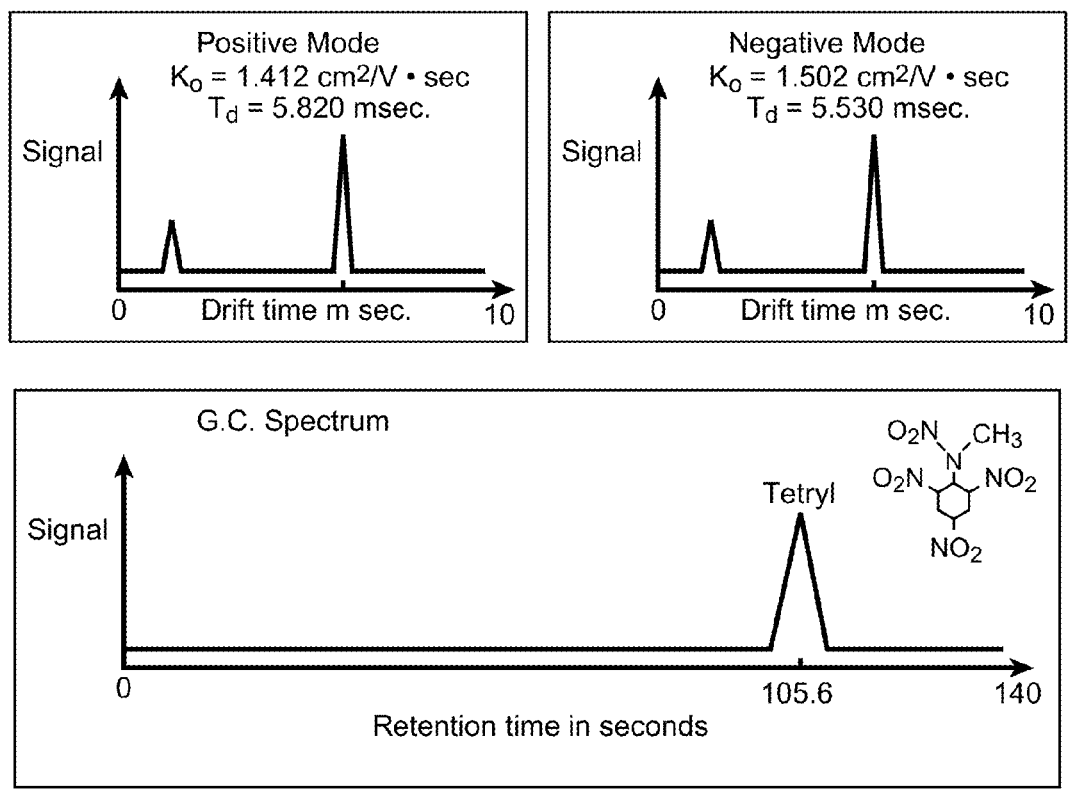
FIG. 7 shows a sample detector output display.

FIG. 7 shows, by way of example, the output and display associated with selective detection of the explosive Tetryl. In the preferred embodiment, the generated positive and negative ions for specific GC peak are averaged and displayed in a plot of ions intensity versus drift time in milliseconds and separation time in seconds. Tetryl is an example of a substance that forms both negative and positive ions for a single GC peak. Tetryl is separated at retention time of 105.6 seconds and produced a positive ion peak at drift time 5.82 milliseconds and reduced mobility constant of $1.412$ $cm^2$/V.sec. The negative ion detected at the same retention time at drift time of 5.53 msec and reduced mobility constant 1.502 cm2/V.sec. More generally, the detection algorithm used by the system 10 (and executed by the microprocessor) identifies the substance or analyte based on retention time, specific reduced mobility constants and the ratio of the positive and negative ion signals for specific analyte.

It will be appreciated by those skilled in the art that system 10 is preferably programmed to detect specific, pre-determined substances, or analytes of interest. It is thus known in advance, which potential analytes of interest are sought to be detected. For each analyte of interest, basic properties such as boiling point, retention time, reduced mobility, drift time and ion intensity are known in advance. This allows the pre-separator 16, GC 18, IMS 20 and microprocessor to detect and identify the pre-determined analytes of interest.

The invention claimed is:

1. A system for detecting the presence of a plurality of predetermined analytes in a sample, the system comprising:
   a temporal separation means for temporally separating the predetermined analytes, contained within the sample, from one another;
   an ion mobility spectrometer detector programmed to detect the predetermined analytes in the sample;
   wherein the temporal separation means is configured to deliver the predetermined analytes one by one, separated from one another in time, to the ion mobility spectrometer detector.

2. A system as claimed in claim 1, wherein the system further comprises a means for pre-conditioning the sample by removing volatile compounds from the sample and delivering the pre-conditioned sample to the temporal separation means.

3. A system as claimed in claim 2, wherein the temporal separation means comprises a pre-separator and a gas chromatograph.

4. A system as claimed in claim 2, wherein the pre-conditioning means comprises a desorber configured to ramp up temperature to first release and remove the volatile compounds, and then evaporate the sample, to produce the pre-conditioned sample.

5. A system as claimed in claim 1, wherein the temporal separation means comprises a pre-separator for separating the predetermined analytes, and a GC for further separating the predetermined analytes.

6. A system as claimed in claim 5, wherein the GC is configured to ramp the temperature of the sample to separate the predetermined analytes deliver the predetermined analytes one by one, separated in time, to the ion mobility spectrometer detector.

7. A method of detecting the presence of a plurality of predetermined analytes in a sample, the method comprising the steps of:
   temporally separating potential predetermined analytes in the sample from one another;
   delivering the temporally separated potential predetermined analytes one-by-one, separated in time from one another, to an ionization chamber of an IMS detector;
   deploying chemical ionization reagent to the ionization chamber concurrently with the delivery of each potential predetermined analyte;
   withholding chemical ionization reagent when there is no delivery of predetermined analyte to the ionization chamber occurring;
   if one or more predetermined analytes is present, detecting their presence.

8. A method as claimed in claim 7, wherein the delivery step comprises outputting a potential predetermined analyte from a GC in association with a GC peak.

9. A detector for detecting the presence a plurality predetermined analytes in a sample, the detector comprising an IMS detector configured receive potential predetermined analytes from a GC during GC peaks, the detector being configured to simultaneously ionize the potential predetermined analytes positively and negatively, and to scan across the GC peaks one by one to obtain both positive and negative scans across each GC peak.

10. A detector as claimed in claim 9, wherein the IMS detector includes a single high voltage power supply and a switch for switching the polarity of the power supply back and forth between positive and negative.

11. A detector as claimed in claim 9, wherein the IMS detector includes a positive high voltage power supply and a negative high voltage power supply, and a switch to switch between the two power supplies so as to switch the detector polarity back and forth between positive and negative.

* * * * *